United States Patent [19]

Inoue et al.

[11] Patent Number: 5,254,721
[45] Date of Patent: Oct. 19, 1993

[54] PROCESS FOR PRODUCING CYCLOHEXYL ACETATE

[75] Inventors: Kaoru Inoue; Masao Iwasaki; Kazuaki Matsui, all of Kanagawa, Japan

[73] Assignee: Mitsui Toatsu Chemicals, Incorporated, Tokyo, Japan

[21] Appl. No.: 597

[22] Filed: Jan. 5, 1993

Related U.S. Application Data

[63] Continuation of Ser. No. 709,983, Jun. 4, 1991, abandoned.

[30] Foreign Application Priority Data

Jun. 11, 1990 [JP] Japan .................................. 2-149965
Jun. 15, 1990 [JP] Japan .................................. 2-155253

[51] Int. Cl.⁵ ........................ C07C 69/02; C07C 67/00
[52] U.S. Cl. ..................................... 560/231; 560/241
[58] Field of Search ............................... 560/231, 241

[56] References Cited

U.S. PATENT DOCUMENTS 3,228,971  1/1966  MacLean ........................ 260/465.4
3,644,497  2/1972  Mesich ............................. 260/497 R
3,696,142  10/1972 Schulz et al. .................... 260/488 R
4,205,182  5/1980  Izumi et al. ........................ 560/247

FOREIGN PATENT DOCUMENTS 2022349   7/1970  France .
4024476   7/1969  Japan ................................. 560/241
48-39425  6/1973  Japan .
53-6131   3/1978  Japan .
4-316535  11/1992 Japan .

Primary Examiner—José G. Dees
Assistant Examiner—Porfirio Nazario-Gonzalez
Attorney, Agent, or Firm—Burns, Doane, Swecker & Mathis

[57] ABSTRACT

Cyclohexyl acetate is produced by reacting acetic acid with cyclohexene in the presence of a heteropolyacid mainly composed of oxides of tungsten as a catalyst. The heteropolyacid may have water of crystallization adjusted to the amount of average 3.0 molecules or less per one molecule of the heteropolyacid. Cyclohexyl acetate can be produced in high selectivity and high conversion. The catalyst is effective even at a low temperature and stable even at a high temperature.

18 Claims, No Drawings

PROCESS FOR PRODUCING CYCLOHEXYL ACETATE

This application is a continuation of application Ser. No. 07/709,983, filed Jun. 4, 1991, now abandoned.

BACKGROUND OF THE INVENTION

1. Field of the Invention

The present invention relates to a process for producing cyclohexyl acetate, and more particularly, to a process for producing cyclohexyl acetate by the reaction of acetic acid with cyclohexene in the presence of heteropolyacids mainly composed of oxides of tungsten.

2. Description of the Related Art

Heretofore, as processes for producing cyclohexyl acetate, there have been generally known an esterification method of acetic acid with cyclohexanol and a reaction of cyclohexanol with acetic anhydride.

However, both processes use cyclohexanol as a starting material, and cyclohexanol has a problem as to the method for preparation thereof and other various drawbacks. In addition, the esterification reaction is an equilibrium reaction so that it is difficult to produce the ester in high yield and moreover it is necessary for removing the water as a by-product in order for the reaction to proceed.

In the method of using acetic anhydride, although the yield of the ester is high, there are many various drawbacks, for example: acetic anhydride is expensive and in addition, one molecule of acetic acid is released and it is very difficult to convert the acetic acid into the anhydride.

For the purposes of solving these problems, some methods for producing cyclohexyl acetate by an addition reaction of cyclohexene with acetic acid have been recently proposed. For example, Japanese Patent Application Laid-open No. 254634/1989 discloses a method for producing cyclohexyl acetate by the reaction of cyclohexene with acetic acid in the presence of a strongly acidic cation exchange resin as a catalyst.

According to this method, the reaction should be effected at 130° C. for 5 hours. However, in general, the heat resistant temperature of such strongly acidic cation exchange resins are inherently about 100° C., and even highly heat resistant resins can not withstand a temperature higher than 160° C. Therefore, when such ion exchange resins are used, a high reaction temperature and a long reaction time are required. In addition, these ion exchange resins have also drawbacks that the mechanical strength is low and the resins are easily broken so that the stability as a catalyst is unreliable to a great extent and further the catalytic activity is low.

Japanese Patent Application Laid-open No. 313447/1989 discloses an addition reaction of acetic acid with cyclohexene in the presence of both ZSM-5, a high silica content-zeolite, as a catalyst and water. According to this method, the reaction temperature is 120° C. and the reaction time is 4 hours resulting in the formation of cyclohexanol in a 12.5% yield and cyclohexyl acetate at most in a 65% yield. The reaction temperature is high and the catalytic activity is low.

The present inventors have conduct research on efficient methods for the production of cyclohexyl acetate, and noted that the addition reaction of cyclohexene with acetic acid is an excellent method for producing cyclohexyl acetate and have considered the conventional drawbacks such as low catalytic activity, and low durability as catalyst including low mechanical strength and low heat resistance. As a result, the present invention has been completed.

SUMMARY OF THE INVENTION

It is an object of the present invention to provide a process for producing efficiently cyclohexyl acetate.

It is another object of the present invention to provide a catalyst useful for producing cyclohexyl acetate from cyclohexene and acetic acid.

It is a further object of the present invention to provide a catalyst for producing cyclohexyl acetate in high conversion and high selectivity within a short time.

It is still another object of the present invention to provide a catalyst for producing cyclohexyl acetate effectively at a low temperature region.

It is a still further object of the present invention to provide a catalyst capable of producing cyclohexyl acetate stably even at a high temperature region. According to the present invention, there is provided a process for producing cyclohexyl acetate which comprises reacting acetic acid with cyclohexene in the presence of at least one heteropolyacid mainly composed of oxides of tungsten.

DESCRIPTION OF THE PREFERRED EMBODIMENTS

In the above-mentioned present invention, the heteropolyacids mainly composed of oxides of tungsten used as catalysts are preferably a heteropolyacid of the formula, $$(M_1)_a(M_2)_b(W)_c(O)_d(H)_e$$

where $M_1$ and $M_2$ are independently metal elements, W is tungsten, O is oxygen, H is hydrogen, a is an integer of 1 or 2, b is an integer of 0, 1 or 2, c is a positive integer of 20 or less, d is a positive integer of 100 or less, and e is a positive integer of 10 or less.

In the above-mentioned formula, preferably $M_1$ is an element selected from the group consisting of P, Si, Co, Mn, Ni, As, Ti, Fe, V and B, and $M_2$ is V. More preferably, the heteropolyacid is tungstophosphoric acid and/or tungstosilic acid. The most easily available heteropolyacids are, for example, dodecatungstosilicic acid ($SiW_{12}O_{40}H_4$), heteropolyacids produced by replacing one or more of tungsten atoms of dodecatungstosilicic acid with vanadium atom(s), dodecatungstophosphoric acid ($PW_{12}O_{40}H_4$), and heteropolyacids produced by replacing one or more of tungsten atoms with vanadium atom(s), and the like. However, the process of the present invention is not limited to these heteropolyacids.

The heteropolyacids mainly composed of oxides of tungsten may be those containing no water of crystallization and/or those containing water of crystallization in the process of the present invention. It is more preferable that the heteropolyacids mainly composed of oxides of tungsten have water of crystallization adjusted to an amount on average of 3.0 molecules or less per one molecule of the heteropolyacid In addition, it is much more preferable in the process of the present invention to use a heteropolyacid mainly composed of oxides of tungsten wherein the amount of water of crystallization is an average of 3.0 molecules or less per one molecule of the heteropolyacid resulting from adjusting the amount of said water by heating a heteropolyacid mainly composed of tungsten oxide at a temperature range of from 150° C. to 500° C., or by heating a heteropolyacid mainly composed of tungsten oxide in a stream of a gas inert to the heteropolyacid.

When the process of the present invention is carried out in the presence of the heteropolyacid the amount of water of crystallization of which has been adjusted to 3.0 molecules or less per one molecule of the heteropolyacid, it is preferable that the amount of water other than water of crystallization of the heteropolyacid in the reaction system is 30.0 molecules or less per one molecule of the heteropolyacid In the present invention, it is not particularly necessary to purify the starting materials, that is, acetic acid and cyclohexene, and commercially available acetic acid and cyclohexene of chemical reagent grade may be used as they are. It is preferable to remove water.

Heteropolyacids mainly composed of oxides of tungsten usually contain water of crystallization. In the present invention, "water of crystallization" of the heteropolyacids is a general term for water contained in heteropolyacids when they are prepared or commercially sold.

Concretely it is, for example, water attached to or taken in heteropolyacid crystals when heteropolyacids are prepared in a water-containing solvent and then precipitated by using a non-solvent or the like, or water taken in heteropolyacide by adsorption, deliquescence or the like.

For example, a commercially available dodecatungstosilicic acid can be represented by the general formula, $H_4SiW_{12}O_{40} \cdot nH_2O$ and a commercially available dodecatungstophosphoric acid can be represented by the general formula, $H_3PW_{12}O_{40} \cdot nH_2O$. Water of crystallization is the $n \cdot H_2O$, and represents water molecules taken in or adsorbed to or contained in the crystal structure.

Therefore, in the process of the present invention the heteropolyacids represented by the above-mentioned general formulas indicate that they have n molecules of water of crystallization. The n is an average value so that it is not always an integer, but a real number. The n of commercially available heteropolyacids usually ranges from about 25 to about 30. The n can be more than these values due to the adsorption of water or the like.

Water of crystallization contained in those heteropolyacids can be easily reduced i.e. the value of n can be decreased, by a dehydration treatment such as heating and the like, and it is also possible to reduce the value of n to zero. In addition, it is also possible to increase the value of n by causing the dehydrated heteropolyacid to adsorb water.

According to the following methods, water of crystallization contained in heteropolyacids mainly composed of oxide of tungsten used as a catalyst for the process of the present invention may be reduced to 3 molecules or less per one molecule of the heteropolyacid.

Easily available heteropolyacids mainly composed of oxide of tungsten usually contain several tens of moles of water of crystallization. A method for reducing the water of crystallization to an average of 3 molecules or less per one molecule of the heteropolyacid is not particularly limited in the present invention, but as an easily operable method, there may be mentioned a dehydration treatment by heating etc.

As the dehydration treatment by heating, for example, heating in an ordinary electric furnace (muffle furnace) is recommended. Naturally, according to the present invention, the method is not limited to the heating by this apparatus.

Neither is the heating temperature particularly limited and any temperature may be used as far as water of crystallization can be reduced to an average of 3.0 molecules or less per one molecule of the heteropolyacid, but for the effective operation, it is preferable to effect the procedure at a temperature of 80° C.-500° C., more preferably, 200° C.-450° C. At a lower temperature, the dehydration is difficult while heteropolyacid anhydride is formed at 550° C. or higher.

The heating time is not particularly limited as long as the amount of water of crystallization is in the above-mentioned range. For example, when an ordinary electric furnace is used and the dehydration is conducted at about 300° C., the above-mentioned range of the amount of water of crystallization can be sufficiently attained in about 3 hours. When, as a catalyst, a heteropolyacid is used which is prepared by heating and dehydrating the heteropolyacid in an inert gas flow at the heat-dehydrating temperature and controlling the amount of water of crystallization to an average of 3.0 molecules or less per one molecule of the heteropolyacid, the activity of the resulting catalyst is much higher. This operation can provide a very effective catalyst.

The gas used in the heat-dehydration operation may be any gas as long as it is inert to the heteropolyacid mainly composed of oxide of tungsten at the heating temperature.

In addition, even if the gas is liquid or solid at ordinary temperature, it may be used, provided that it is in a gaseous state at the heating temperature and inert to the heteropolyacid.

Exemplary suitable gases include air, argon, nitrogen, helium, hydrogen, aliphatic hydrocarbons, aromatic hydrocarbons and the like, but naturally are not limited thereto. In addition, the flow rate of inert gas is not critical, but the space velocity in the apparatus in terms of gas volume at the heating temperature is preferably 0.2-20 vol/hr.vol.

According to the process of the present invention, even when the heteropolyacid contains 20-30 molecules of water of crystallization per one molecule of the heteropolyacid which are ordinary amounts of water of crystallization of the heteropolyacid, it exhibits a good catalytic activity.

However, when the amount of water is controlled to an average of 3.0 molecules or less per one molecule of the heteropolyacid by dehydration or the like, the resulting heteropolyacid exhibits a particularly high catalytic activity. In addition, since this catalyst is thermally very stable, the process of the present invention can be sufficiently stably carried out at an elevated temperature.

According to the process of the present invention, the reaction of acetic acid with cyclohexene to form cyclohexyl acetate proceeds as an addition reaction. The reaction may be carried out in a liquid phase homogeneous system, or in a solid phase-gas phase or a solid phase-liquid phase heterogeneous system or the like.

The process of the present invention may be effected under any pressure condition such as ambient pressure, reduced pressure, and elevated pressure. When the reaction is effected at a high temperature, a liquid phase reaction may be conducted at an elevated pressure. The operation type of reaction is not particularly limited, and any of continuous system, batch system and semi-batch system may be employed.

It is possible to add a inert solvent or a diluent to the catalyst and the reaction agents (starting materials and the product).

Inert solvents or diluents may be added to the catalyst and reaction agents (the starting materials and product).

Exemplary suitable inert solvents and diluents include aliphatic saturated hydrocarbons such as n-butane, n-pentane, n-hexane, n-heptane, n-octane, n-nonane, n-decane, isomers thereof and the like; aromatic hydrocarbons such as benzene, toluene, ethylbenzene, xylene, anisole, cumene, nitrobenzene and the like; alicyclic saturated-hydrocarbons such as cyclopentane, alkyl-substituted cyclopentanes, alkoxy-substituted cyclopentanes, nitro-substituted cyclopentanes, cyclohexane, alkyl-substituted cyclohexanes, alkoxy-substituted cyclohexanes, nitro-substituted cyclohexanes, cycloheptane, alkyl-substituted cycloheptanes, alkoxy-substituted cycloheptanes, nitro-substituted cycloheptanes, cyclooctane, alkyl-substituted cyclooctanes, alkoxysubstituted cyclooctanes, nitro-substituted cyclooctanes and the like; nitrogen, air, argon, helium and the like.

When the reaction is carried out at an elevated pressure, it is possible to pressurize inert nitrogen, argon or the like into the reaction agents and catalyst in advance and carry the reaction in a liquid phase reaction system.

In the process of the present invention, the ratio of acetic acid to cyclohexene charged upon effecting the reaction are not particularly limited The molar ratio of acetic acid to cyclohexene is usually in the range of from 0.1 to 100. For example, in order to attain a high conversion of acetic acid, it is desirable to conduct the reaction at a molar ratio of acetic acid to cyclohexene of less than 1 while in order to attain a high conversion of cyclohexene, it is desirable to effect the reaction at a molar ratio of acetic acid to cyclohexene of more than 1.

For carrying out the process of the present invention, the amount of the catalyst to be added is not particularly critical, but it is advisable in the case of the reaction in a batch system to use the catalyst in an amount of 0.1-100% by weight, preferably 1-50% by weight based on the weight of cyclohexene fed.

When the amount of the catalyst is less than the above-mentioned amount, the reaction proceeds slowly while at the amount exceeding an above-mentioned amount the reaction proceeds sufficiently, but it is not preferable from an economical point of view. However, the process of the present invention naturally can be effected outside of the above-mentioned range.

Upon carrying out the process of the present invention, the manner in which the catalyst and reaction agents are fed is not particularly limited. The catalyst, acetic acid and cyclohexene may be simultaneously fed, and the catalyst may be dissolved or suspended in a solvent or the like and then fed to a reaction vessel. In addition, there are various methods, for example, before the reaction, acetic acid and the catalyst are mixed in advance and then cyclohexene is added, or the catalyst and cyclohexene are mixed and then acetic acid is added.

Upon effecting the process of the present invention, when the heteropolyacid catalyst mainly composed of oxide of tungsten contains an average of 3.0 molecules of water of crystallization or less per one molecule of the heteropolyacid, the water amount in the reaction system particularly affects the reaction.

In particular, in order to obtain a catalytic activity higher than that of commercially available heteropolyacid containing several tens of molecules of water of crystallization per one molecule of the heteropolyacid, it is necessary to control the amount of water other than water of crystallization contained in the heteropolyacid to 30 molecules or less per one molecule of the heteropolyacid used.

When the amount of water is higher than that, dehydration of water of crystallization in the heteropolyacid fails to give an effective result.

In such a case, the water content in the above-mentioned acetic acid and cyclohexene is at most 100 ppm so that when the amount of the catalyst added to the reaction system is on the order of percent based of the reaction system, the amount of water (excluding water of crystallization) in the reaction system does not exceed the above-mentioned value in case that commercially available acetic acid and cyclohexene are used in the process of the present invention.

The reaction temperature in the process of the present invention is not particularly limited, but the reaction may be effected at a wide range of temperature. It is preferably 0° C.–400° C., more preferably 30° C.–200° C. If the reaction temperature is too low, the reaction velocity is lowered. On the contrary, if the reaction temperature is too high, reaction agents such as cyclohexene and the like are liable to be thermally deteriorated and thereby such a high temperature is not economical.

The reaction time varies depending upon the catalyst amount or reaction temperature. When the catalyst amount is large and the temperature is high, the reaction time is very short, for example, about 0.1 sec. or less. On the contrary, when the catalyst amount is small and the temperature is low the reaction time is long, for example, about 24 hours.

After completion of the reaction, the end product can be recovered by an ordinary separation procedure such as distillation and the like.

Examples of various methods for carrying out the process of the present invention are as shown below. The methods are not critical, but the following are some examples of easily operable methods though the present invention is not limited thereto.

(1) In a glass flask equipped with a stirrer are placed prescribed amounts of the catalyst, acetic acid and cyclohexene, if desired, together with a diluent such as a solvent and the like and if necessary, a reflux condenser is fitted to the flask, and then the reaction is effected by heating with stirring.

(2) Prescribed amounts of the catalyst, acetic acid and cyclohexene are added to an autoclave, if desired, together with a medium such as nitrogen, argon and the like, and then the heating reaction is conducted with stirring.

(3) Into a reactor previously kept at a prescribed temperature and pressure are continuously introduced prescribed amounts of the catalyst, cyclohexene and acetic acid, if desired, together with a diluent such as a solvent and the like to carry out the reaction.

According to the process of the present invention, cyclohexyl acetate can be prepared very efficiently by an addition reaction of acetic acid with cyclohexene in the presence of a heteropolyacid mainly composed of oxides of tungsten, and further, drawbacks of conventional catalysts such as low catalytic activity, low heat resistance and the like can be solved, for example, the catalyst in the present invention is effective even at low temperatures and stable even at high temperatures.

In particular, when the amount of water of crystallization of the heteropolyacid is controlled to an average of 3 molecules or less per one molecule of the heteropolyacid, the reaction exhibits a very high reaction efficiency. Even under very mild conditions such as low temperature and within a short time, for example, about one hour, cyclohexyl acetate can be produced in high selectivity and in high conversion.

Moreover, even under high temperature conditions, the process can be stably and effectively carried out.

Cyclohexyl acetate may be used as a starting material for cyclohexanol which is useful as an intermediate of phenol, nylon and adipic acid and may be used as a cycloalkanol carboxylic acid ester useful as a special solvent.

The present invention is explained in the following more in detail referring to examples.

Legend in the following tables:

| Cy - Hex | Cyclohexene |
| Cy - HexOAc | Cyclohexyl acetate |
| Ar | Argon |
| He | Helium |

(1) Quantitative Measurement of the Reaction Product: After conducting the reaction for a prescribed time at a prescribed temperature, the reaction liquid was cooled to room temperature and subjected to gas chromatography to measure the reaction product quantitatively.

(2) Quantitative Measurement of Water of Crystallization contained in the catalyst:

The amount of water of crystallization contained in the heteropolyacid mainly composed of oxide of tunsten was determined based on an anhydrous heteropolyacid (the amount of water of crystallization being zero) produced by heating and dehydrating the heteropolyacid at 500° C. until the weight became constant and did not decrease any more.

EXAMPLE 1

To a 70 ml three-necked flask equipped with a magnetic stirrer and a reflux condenser were added a commercially available dodecatungstophosphoric acid ($H_4PW_{12}O_{40}$, $28H_2O$) 2.0 g, a commercially available 99.5% acetic acid (manufactured by Kokusan Kagaku K. K, special grade) 20.5 g and a commercially available 98% cyclohexene (manufactured by Tokyo Kasei K. K., special grade) 4.5 g, and the flask was placed in an oil bath and heated at 70° C. for 1.5 hours with stirring to effect the reaction.

After the procedure, stirring was stopped and the flask was taken out of the oil bath and cooled to room temperature, and then the reaction liquid was quantitatively analyzed.

The result is as shown in Table 1, that is, the yield of cyclohexyl acetate was 33.4% (selectivity being 97.3%) and conversion of cyclohexene was 34.3%.

COMPARISON EXAMPLE 1

The procedure of Example 1 was repeated under the same reaction conditions except that 2.0 g of H-ZSM5 zeolite was used as a catalyst in place of dodecatungstophosphoric acid, but cyclohexyl acetate was not formed and the starting materials, cyclohexene and acetic acid were recovered.

EXAMPLE 2

The procedure of Example 1 was repeated to produce cyclohexyl acetate from cylohexene and acetic acid under the same conditions except that the reaction time was 3 hours. As a result, the amount of the product, cyclohexyl acetate increased as the reaction time increased as shown in Table 1.

EXAMPLE 3

The procedure of Example 1 was repeated to carry out the reaction of acetic acid and cyclohexene under the same conditions including catalyst amount except that the catalyst was replaced with a commercially available dodecatungstosilicic acid ($H_4SiW_{12}O_{40}$, $25H_2O$). The result is as shown in Table 1.

EXAMPLE 4

The procedure of Example 3 was repeated except that the reaction time was 3 hours and the reaction of acetic acid with cyclohexene was conducted.

EXAMPLE 5

In a 200 ml autoclave were placed the above-mentioned commercially available dodecatungstosilicic acid 5.0 g, the above-mentioned commercially available acetic acid 61.5 g and the above-mentioned commercially available cyclohexene 13.5 g and nitrogen gas was fed thereinto until the pressure reached 5 $kg/cm^2$ (gauge), and then a reaction was carried out with stirring by heating at 100° C. for 1 hour. The result is shown in Table 1, that is, cyclohexyl acetate was produced in high yield.

TABLE 1

|  | Cy - Hex | Cy - HexOAc | |
|---|---|---|---|
|  | Conversion (%) | Yield (%) | Selectivity (%) |
| Example 1 | 34.3 | 33.4 | 97.3 |
| Example 2 | 50.6 | 50.2 | 99.2 |
| Example 3 | 57.2 | 54.8 | 95.8 |
| Example 4 | 71.2 | 71.2 | 100.0 |
| Example 5 | 88.1 | 87.6 | 99.4 |

EXAMPLE 6

Preparation of dehydrated dodecatungstophosphoric acid catalysts by heating

As shown in Table 2 (infra), the above-mentioned commercially available dodecatungstophosphoric acid was heated and dehydrated in an electric furnace (muffle furnace) at a prescribed temperature for a prescribed time. As a result, the compositions of water of crystallization in dodecatungstophosphoric acid are as shown in Table 2 (infra). The number of molecule of water of crystallization per one molecule of the dodecatungstophosphoric acid thus dehydrated is designated as n' in the table.

TABLE 2

|  | Heating temperature (°C.) | Heating time (hr.) | n' |
|---|---|---|---|
| Catalyst 1 | 350 | 3.0 | 0 |
| Catalyst 2 | 400 | 3.0 | 0 |
| Catalyst 3 | 300 | 3.0 | 0 |
| Catalyst 4 | 250 | 1.0 | 1.4 |
| Catalyst 5 | 250 | 0.5 | 3.0 |
| Catalyst 6 | 200 | 0.25 | 4.8 |

TABLE 2-continued

| | Heating temperature (°C.) | Heating time (hr.) | n' |
|---|---|---|---|
| Catalyst 7 | 120 | 1.0 | 8.0 |

EXAMPLE 7

The reaction of acetic acid with cyclohexene was effected by using the same apparatus as that of Example 1 and under the same conditions as those of Example 1 except that the above-mentioned catalyst 1 was used as a heteropolyacid. As shown in Table 3, the catalytic activity was markedly improved.

EXAMPLE 8

The reaction of acetic acid with cyclohexene was conducted using the same apparatus and conditions as those of Example 7 except that the above-mentioned catalyst 2 was used as a heteropolyacid catalyst. As shown in Table 3, when the dehydration temperature for preparing the catalyst was elevated, the catalyst activity was hardly affected and it was confirmed that the catalyst activity was very high.

EXAMPLE 9

The reaction of Example 7 was repeated except that catalyst 3 was used. As shown in Table 3, the reaction result was similar to those for catalyst 1 and catalyst 2. The facts in Examples 7-9 show that the amount of water of crystallization of a heteropolyacid is more important than the dehydration temperature so as to improve remarkably the activity of the catalyst by dehydrating the heteropolyacid mainly composed of oxides of tungsten.

EXAMPLE 10

The procedure of Example 7 was repeated except that catalyst 4 was used as a catalyst. The result is shown in Table 3.

EXAMPLE 11

The procedure of Example 7 was repeated except that catalyst 5 was used as a catalyst. The result is shown in Table 3.

EXAMPLE 12

The reaction of acetic acid with cyclohexene was conducted under the same conditions as in Example 7 except that catalyst 6 was used as a catalyst. As is clear from the result shown in Table 3, an improvement in catalytic activity due to dehydration of the heteropolyacid was not observed.

EXAMPLE 13

The reaction was conducted under the same conditions as in Example 7 except that catalyst 7 was used as a catalyst. As is clear from the result shown in Table 3, the catalyst exhibited a catalytic activity similar to that of a commercially available dedecatungstophosphoric acid.

EXAMPLE 14

The reaction of acetic acid with cyclohexene was conducted under the same conditions as in Example 7 except that 0.5 g of catalyst 1 was used which was a reduced amount as compared with 2 g in Example 7. The result is shown in Table 3.

EXAMPLE 15

The reaction was conducted under the same conditions as in Example 14 except that the reaction time was 3 hours. As is clear from the result shown in Table 3, as the reaction time increased, the amount of produced cyclohexyl acetate increased and no deterioration of the catalyst occurred.

EXAMPLE 16

To a 200 ml autoclave were added 2.0 g of catalyst 1, 61.5 g of acetic acid and 13.5 g of cyclohexene, and nitrogen gas was fed to the autoclave until the pressure reached 5 kg/cm$^2$ (gauge), and then, the cyclohexyl acetate producing reaction was conducted at 100° C. for 1 hour. The result is shown in Table 3.

EXAMPLE 17

The procedure of Example 16 was repeated to conduct the reaction of acetic acid with cyclohexene except that the reaction temperature was 130° C. and the reaction time was 0.5 hour. The result is shown in Table 3, that is, cyclohexyl acetate was produced in high yield within a short time.

TABLE 3

| | Catalyst | n' | Cy - Hex Conversion (%) | Cy - HexOAc Yield (%) | Cy - HexOAc Selectivity (%) |
|---|---|---|---|---|---|
| Example 7 | 1 | 0 | 81.7 | 80.6 | 97.3 |
| Example 8 | 2 | 0 | 80.9 | 80.5 | 99.5 |
| Example 9 | 3 | 0 | 81.2 | 80.5 | 99.1 |
| Example 10 | 4 | 1.4 | 82.6 | 80.8 | 97.8 |
| Example 11 | 5 | 3.0 | 70.5 | 68.0 | 96.5 |
| Example 12 | 6 | 4.8 | 9.4 | 8.9 | 94.9 |
| Example 13 | 7 | 8.0 | 37.1 | 35.1 | 94.5 |
| Example 14 | 1 | 0 | 41.3 | 40.2 | 97.4 |
| Example 15 | 1 | 0 | 63.4 | 62.3 | 98.2 |
| Example 16 | 1 | 0 | 89.5 | 88.9 | 99.3 |
| Example 17 | 1 | 0 | 91.2 | 90.4 | 99.1 |

The amount of catalyst in each of the Examples other than Examples 14 and 15 was 2.0 g, and that in each of Examples 14 and 15 was 0.5 g. n' denotes the number of molecules of water of crystallization contained in one molecule of the dehydrated heteropolyacid, the catalyst.

EXAMPLE 18

Preparation of dehydrated heteropolyacid catalyst

The above-mentioned commercially available dodecatungstosilicic acid (containing 25 molecules of water of crystallization per one molecule of the heteropolyacid) was placed in a muffle furnace and subjected to heating and dehydration at the prescribed temperature for the prescribed time as shown in Table 4. The number of molecules of water of crystallization contained in the dodecatungstosilicic acid thus dehydrated per one molecule of said heteropolyacid is designated as n', which is shown in Table 4.

TABLE 4

| | Heating temperature (°C.) | Heating time (hr.) | n' |
|---|---|---|---|
| Catalyst 8 | 370 | 3.0 | 0 |
| Catalyst 9 | 420 | 1.0 | 0 |
| Catalyst 10 | 300 | 3.0 | 0 |
| Catalyst 11 | 250 | 2.0 | 1.7 |
| Catalyst 12 | 250 | 0.75 | 3.0 |
| Catalyst 13 | 250 | 0.5 | 4.0 |
| Catalyst 14 | 180 | 0.25 | 5.8 |

TABLE 4-continued

| | Heating temperature (°C.) | Heating time (hr.) | n' |
|---|---|---|---|
| Catalyst 15 | 150 | 0.75 | 12.7 |
| Catalyst 16 | 100 | 1.0 | 21.5 |

EXAMPLE 19

The reaction of acetic acid with cyclohexene was conducted by repeating the procedure of Example 3 except that catalyst 8 (2.0 g fed) was used in place of the commercially available dodecatungstosilicic acid. As is clear from the result shown in Table 5, a very high catalytic activity was observed.

EXAMPLE 20

The procedure of Example 19 was repeated except that catalyst 9 was used in place of said catalyst. As is clear from the result shown in Table 5, the reaction result was hardly affected by elevating the dehydration temperature.

EXAMPLE 21

The procedure of Example 19 was repeated except that catalyst 10 was used in place of said catalyst. As is clear from the result shown in Table 5, the reaction result was hardly affected by lowering the dehydration temperature upon preparing the catalyst.

EXAMPLE 22

The reaction of acetic acid with cyclohexene was conducted under the same conditions as in Example 19 except that catalyst 11 was used. The result is shown in Table 5.

EXAMPLE 23

The procedure of Example 19 was repeated except that catalyst 12 was used. The result is shown in Table 5.

EXAMPLE 24

The cyclohexyl acetate production reaction was conducted by repeating the procedure of Example 19 except that catalyst 13 was used. The result is shown in Table 5.

EXAMPLE 25

The procedure of Example 19 was repeated except that catalyst 14 was used. As is clear from the result shown in Table 5, the reaction result was lowered in a similar manner to Example 24.

EXAMPLE 26

The procedure of Example 19 was repeated except that catalyst 15 was used. As is clear from the result shown in Table 5, any catalyst activation effect due to the dehydration of the heteropolyacid was not recognized.

EXAMPLE 27

The procedure of Example 19 was repeated except that catalyst 16 was used. As shown in Table 5, an effect due to the dehydration of the heteropolyacid was not recognized.

In view of the results of Examples 19-27, it is noted that when the amount of water, of crystallization contained in a heteropolyacid is 3.0 molecules or less per one molecule of the heteropolyacid, the heteropolyacid exhibits a very high catalytic activity in the cyclohexyl acetate forming reaction of acetic acid with cyclohexene.

EXAMPLE 28

The procedure of Example 19 was conducted except that 0.5 g of catalyst 8 was used. The result is shown in Table 5.

EXAMPLE 29

The procedure of Example 28 was repeated except that the reaction time was 3 hours. As is clear from the result shown in Table 5, as the reaction increases, the amount of cyclohexyl acetate produced increases, and this fact indicates that the catalyst is not deteriorated.

EXAMPLE 30

To a 200 ml autoclave were added 2.0 g of catalyst 8, 61.5 g of acetic acid, 13.5 g of cyclohexene, and nitrogen gas was fed into the autoclave until the pressure reached 5 kg/cm$^2$ (gauge), and then the cyclohexyl acetate production reaction was carried out at 100° C. for one hour. The result is shown in Table 5.

EXAMPLE 31

The procedure of Example 24 was repeated except that the reaction temperature was 130° C. and the reaction time was 0.5 hour. The result is shown in Table 5. It indicates that cyclohexyl acetate was produced in high yield within a short time.

TABLE 5

| | Catalyst | n' | Cy - Hex Conversion (%) | Cy - HexOAc Yield (%) | Cy - HexOAc Selectivity (%) |
|---|---|---|---|---|---|
| Example 19 | 8 | 0 | 87.2 | 86.2 | 98.9 |
| Example 20 | 9 | 0 | 86.8 | 86.0 | 99.1 |
| Example 21 | 10 | 0 | 85.9 | 85.3 | 99.3 |
| Example 22 | 11 | 1.7 | 87.5 | 85.7 | 97.9 |
| Example 23 | 12 | 3.0 | 72.8 | 71.6 | 98.3 |
| Example 24 | 13 | 4.0 | 14.2 | 9.1 | 64.8 |
| Example 25 | 14 | 5.8 | 15.6 | 12.1 | 77.6 |
| Example 26 | 15 | 12.7 | 56.2 | 51.8 | 92.8 |
| Example 27 | 16 | 21.5 | 55.8 | 51.0 | 91.4 |
| Example 28 | 8 | 0 | 43.7 | 42.5 | 97.3 |
| Example 29 | 8 | 0 | 73.8 | 72.9 | 98.9 |
| Example 30 | 8 | 0 | 91.6 | 91.1 | 99.5 |
| Example 31 | 8 | 0 | 95.2 | 94.4 | 99.2 |

The amount of catalyst used in each of Examples other than Examples 28 and 29 was 2.0 g while that in each of Examples 28 and 29 was 0.5 g.

EXAMPLE 32

Preparation of dodecatungstophosphoric Acid Dehydrated Catalyst (2)

The above-mentioned commercially available dodecatungstophosphoric acid was placed in a muffle furnace having an inner volume of 8 liters and wherein a gas or the like can be introduced into and discharged therefrom, and subjected to heating and dehydration at a prescribed temperature for a prescribed time by introducing various gases into the muffle at prescribed flow rates as shown in Table 6. The number of molecules of water of crystallization contained in the tungstophosphoric acid thus treated per one molecule of the tungstophosphoric acid is designated as n' in Table 6.

TABLE 6

| | Gas | Flow rate (Nl/hr.) | Temperature (°C.) | Time (hr.) | n' |
|---|---|---|---|---|---|
| Catalyst 17 | Ar | 5.0 | 350 | 3 | 0 |
| Catalyst 18 | Ar | 5.0 | 400 | 1 | 0 |
| Catalyst 19 | Ar | 5.0 | 300 | 3 | 0 |
| Catalyst 20 | Ar | 5.0 | 250 | 1 | 1.3 |
| Catalyst 21 | Ar | 5.0 | 250 | 0.5 | 2.9 |
| Catalyst 22 | Ar | 35.0 | 350 | 3 | 0 |
| Catalyst 23 | Air | 35.0 | 350 | 3 | 0 |
| Catalyst 24 | He | 35.0 | 350 | 3 | 0 |

TABLE 7

| | Catalyst | n' | Cy-Hex Conversion (%) | Cy-HexOAc Yield (%) | Cy-HexOAc Selectivity (%) |
|---|---|---|---|---|---|
| Example 33 | 17 | 0 | 86.7 | 85.4 | 98.5 |
| Example 34 | 18 | 0 | 85.9 | 85.3 | 99.3 |
| Example 35 | 19 | 0 | 86.2 | 84.6 | 98.1 |
| Example 36 | 20 | 1.3 | 87.6 | 85.0 | 97.1 |
| Example 37 | 21 | 2.9 | 75.8 | 73.3 | 96.7 |
| Example 38 | 22 | 0 | 86.9 | 85.4 | 98.3 |
| Example 39 | 23 | 0 | 87.5 | 85.3 | 97.5 |
| Example 40 | 24 | 0 | 87.2 | 85.8 | 98.4 |

EXAMPLE 33

The reaction of acetic acid with cyclohexene was conducted under the same conditions as in Example 1 except that catalyst 17 (added amount, 2.0g) was used in place of the above-mentioned commercially available dodecatungstophosphoric acid. The result is shown in Table 7. It indicates that the dodecatungstophosphoric acid was converted to a very highly active catalyst by heating and dehydrating dodecatungstophosphoric acid in an argon flow.

EXAMPLE 34

The procedure of Example 33 was repeated except that catalyst 18 was used in place of the catalyst. The result is shown in Table 7.

EXAMPLE 35

The procedure of Example 33 was repeated except that catalyst 19 was used in place of the catalyst. The result is shown in Table 7.

These results indicate that the dehydration temperature hardly affects the catalytic activity.

EXAMPLE 36

The procedure of Example 33 was repeated except that catalyst 20 was used in place of the catalyst. The result is shown in Table 7.

EXAMPLE 37

The procedure of Example 33 was repeated except that catalyst 21 was used in place of the catalyst The result is shown in Table 7.

EXAMPLE 38

The procedure of Example 33 was repeated except that catalyst 22 was used in place of the catalyst The result is shown in Table 7. It indicates that the flow rate of the entering gas does not affect the catalytic activity by comparing the result of Example 38 to that of Example 33.

EXAMPLE 39

The procedure of Example 33 was repeated except that catalyst 23 was used in place of the catalyst The result is shown in Table 7.

EXAMPLE 40

The procedure of Example 33 was repeated except that catalyst 24 was used in place of the catalyst. The result is shown in Table 7. The results in Example 33 - 40 indicate that heating dehydration while passing argon, helium or air is effective.

EXAMPLE 41

Preparation of a catalyst by heating and dehydrating dodecatungstosilicic acid in a gas flow:

In the same muffle furnace as in Example 27 was placed the above-mentioned dodecatungstosilicic acid and a heating and dehydrating treatment was effected at a prescribed temperature for a prescribed time while each gas was passed through the furnace at a prescribed flow rate.

The catalysts thus prepared, preparation conditions, and the number of molecules of water of crystallization (n') per one molecule of the heteropolyacid catalyst thus prepared are shown in Table 8.

TABLE 8

| | Gas | Flow rate (Nl/hr.) | Temperature (°C.) | Time (hr.) | n' |
|---|---|---|---|---|---|
| Catalyst 25 | Ar | 5.0 | 370 | 3 | 0 |
| Catalyst 26 | Ar | 5.0 | 420 | 1 | 0 |
| Catalyst 27 | Ar | 5.0 | 300 | 3 | 0 |
| Catalyst 28 | Ar | 5.0 | 250 | 1 | 1.3 |
| Catalyst 29 | Ar | 5.0 | 250 | 0.5 | 2.9 |
| Catalyst 30 | Ar | 35.0 | 350 | 3 | 0 |
| Catalyst 31 | Air | 35.0 | 350 | 3 | 0 |
| Catalyst 32 | He | 35.0 | 350 | 3 | 0 |

EXAMPLE 42

The reaction of acetic acid with cyclohexene was effected under the same conditions as in Example 3 except that catalyst 25 (added 2.0 g) was used in place of the commercially avilable dodecatungstosilicic acid catalyst. As is clear from the result in Table 9, the tungstosilicic acid catalyst thus heated and dehydrated in argon gas flow has a high catalytic activity.

EXAMPLE 43

The procedure of Example 42 was repeated except that catalyst 26 was used in place of the catalyst. The result is shown in Table 9.

EXAMPLE 44

The procedure of Example 42 was repeated except that catalyst 27 was used in place of the catalyst. The result is shown in Table 9.

EXAMPLE 45

The procedure of Example 42 was repeated except that catalyst 28 was used in place of the catalyst. The result is shown in Table 9.

EXAMPLE 46

The procedure of Example 42 was repeated except that catalyst 29 was used in place of the catalyst. The result is shown in Table 9.

EXAMPLE 47

The procedure of Example 42 was repeated except that catalyst 30 was used in place of the catalyst. The result is shown in Table 9. As is clear from comparison of the result of Example 47 to that of Example 42, when the gas flow amount is changed, the catalytic activity is not affected by the change.

EXAMPLE 48

The procedure of Example 42 was repeated except that catalyst 31 was used in place of the catalyst. The result is shown in Table 9.

EXAMPLE 49

The procedure of Example 42 was repeated except that catalyst 32 was used in place of the catalyst. The result is shown in Table 9.

The results obtained i Examples 42 - 49 show that argon, helium or air is effective as a gas which is passed through the preparation system upon preparing the catalyst by heating and dehydrating.

TABLE 9

| | Catalyst | $n'$ | Cy - Hex Conversion (%) | Cy - HexOAc Yield (%) | Selectivity (%) |
|---|---|---|---|---|---|
| Example 42 | 25 | 0 | 92.6 | 90.5 | 97.8 |
| Example 43 | 26 | 0 | 91.9 | 90.2 | 98.1 |
| Example 44 | 27 | 0 | 90.6 | 90.0 | 99.4 |
| Example 45 | 28 | 1.3 | 92.2 | 90.7 | 98.4 |
| Example 46 | 29 | 2.9 | 77.3 | 74.4 | 96.2 |
| Example 47 | 30 | 0 | 91.8 | 90.2 | 97.7 |
| Example 48 | 31 | 0 | 93.1 | 90.8 | 97.5 |
| Example 49 | 32 | 0 | 91.5 | 90.3 | 98.7 |

EXAMPLE 50

The reaction was conducted by repeating the procedure of Example 33 except that, after feeding the catalyst, acetic acid and cyclohexene, pure water was added such that the water in the reaction system was 1.1 mole per 1 mole of catalyst 17 (water of crystallization being zero). The result is shown is Table 10. In Table 10, the result of Example 33 is also cited for reference.

EXAMPLE 51

The reaction was conducted by repeating the procedure of Example 28 except that pure water was added in a way similar to Example 50 such that the water in the reaction system was 4.5 moles per 1 mole of catalyst 17 (water of crystallization being zero). The result is shown in Table 10.

EXAMPLE 52

The reaction was conducted by repeating the procedure of Example 28 except that pure water was added in a way similar to Example 50 such that the water in the reaction system was 10.2 moles per 1 mole of catalyst 17 (water of crystallization being zero). The result is shown in Table 10.

EXAMPLE 53

The reaction was conducted by repeating the procedure of Example 28 except that pure water was added in a way similar to Example 50 such that the water in the reaction system was 29.2 moles per 1 mole of catalyst 17 (water of crystallization being zero). The result is shown in Table 10.

EXAMPLE 54

The reaction was conducted by repeating the procedure of Example 33 except that pure water was added in a way similar to Example 50 such that the water in the reaction system was 29.2 moles per 1 mole of catalyst 17 (water of crystallization being zero). The result is shown in Table 10. The result of Example 54 shows that an improvement in catalytic activity due to dehydrating the catalyst was not observed.

EXAMPLE 55

The reaction was carried out by repeating the procedure of Example 36 except that, after feeding the catalyst, acetic acid and cyclohexene, pure water was added such that the amount of water other than water of crystallization of catalyst 20 ($n'=1.3$) was 10.2 moles per one mole of the catalyst in the reaction system. The result is shown in Table 10.

EXAMPLE 56

The reaction was carried out under the same conditions as in Example 55 except that catalyst 21 ($n'=2.9$) was used in place of the catalyst. The result is shown in Table 10.

EXAMPLE 57

The reaction was conducted under the same conditions as in Example 42 except that pure water was added in a way similar to Example 50 such that the water amount per one molecule of catalyst 25 (water of crystallization being zero) was 1.1 molecule. The result is shown in Table 10. The result of Example 42 is also listed in Table 10.

EXAMPLE 58

The reaction was carried out under the same conditions as in Example 57 except that he amount of added pure water was 4.5 molecules per one molecule of catalyst 25 (water of crystallization being zero) in place of that in Example 57. The result is shown in Table 10.

EXAMPLE 59

The reaction was carried out under the same conditions as in Example 57 except that the amount of added pure water was 10.5 molecules per one molecule of the catalyst in place of that in Example 57. The result is shown in Table 10.

EXAMPLE 60

The reaction was carried out under the same conditions as in Example 57 except that the amount of added pure water was 29.2 molecules per one molecule of the catalyst in place of that in Example 57. The result is shown in Table 10.

EXAMPLE 61

The reaction was carried out under the same conditions as in Example 57 except that the amount of added pure water was 35.4 molecules per one molecule of the catalyst in place of that in Example 57. The result is shown in Table 10. This indicates that any improvement in the catalytic activity due to the preparation of the catalyst by heating and dehydration was not recognized.

EXAMPLE 62

The procedure of Example 45 was repeated except that the amount of water other than water of crystallization contained in catalyst 28 (n'=1.3) was 10.2 moles per one mole of the catalyst. The result is shown in Table 10.

EXAMPLE 63

The procedure of Example 62 was repeated except that catalyst 29 was used in place of the catalyst. The result is shown in Table 10.

TABLE 10

| | Catalyst | Water (a) | Cy - Hex Conversion (%) | Cy - HexOAc Yield (%) | Selectivity (%) |
|---|---|---|---|---|---|
| Example 33 | 17 | 0.02 | 86.7 | 85.4 | 98.5 |
| Example 50 | 17 | 1.1 | 86.9 | 85.7 | 98.6 |
| Example 51 | 17 | 4.5 | 82.1 | 80.6 | 98.2 |
| Example 52 | 17 | 10.2 | 78.3 | 77.6 | 99.1 |
| Example 53 | 17 | 29.2 | 46.9 | 45.3 | 96.6 |
| Example 54 | 17 | 34.3 | 33.7 | 32.9 | 97.6 |
| Example 55 | 20 | 10.2 | 78.5 | 78.0 | 99.4 |
| Example 56 | 21 | 10.2 | 77.2 | 76.1 | 98.6 |
| Example 42 | 25 | 0.02 | 92.6 | 90.5 | 97.8 |
| Example 57 | 25 | 1.1 | 91.8 | 90.3 | 98.4 |
| Example 58 | 25 | 4.5 | 88.9 | 85.7 | 96.4 |
| Example 59 | 25 | 10.5 | 80.3 | 78.8 | 98.1 |
| Example 60 | 25 | 29.0 | 67.2 | 65.5 | 97.5 |
| Example 61 | 25 | 35.4 | 48.4 | 46.2 | 95.5 |
| Example 62 | 28 | 10.2 | 80.5 | 79.4 | 98.6 |
| Example 63 | 29 | 10.2 | 71.2 | 69.1 | 97.1 |

(a): The number of molecules of water other than water of crystallization of the catalyst present in the reaction system per one molecule of the catalyst.

What is claimed is:

1. A process for producing cyclohexyl acetate which comprises reacting acetic acid with cyclohexene in the presence of at least one heteropolyacid mainly composed of oxides of tungsten which has water of crystallization adjusted to an amount on average of 3.0 moles or less per one molecule of the heteropolyacid.

2. The process according to claim 1 in which the heteropolyacid is heteropolyacid mainly composed of oxides of tungsten containing no water of crystallization.

3. The process according to claim 2 in which the heteropolyacid is mainly composed of oxides of tungsten of the general formula, $$(M_1)_a(M_2)_b(W)_c(O)_d(H)_e$$

where $M_1$ and $M_2$ are independently metal elements, W is tungsten, O is oxygen, H is hydrogen, a is an integer of 1 or 2, b is an integer of 0, 1 or 2, c is a positive integer of 20 or less, d is a positive integer of 100 or less, and e is a positive integer of 10 or less.

4. The process according to claim 3 in which $M_1$ is an element selected from the group of P, Si, Co, Mn, Ni, As, Fe, V, and B, and $M_2$ is V.

5. The process according to claim 1 in which the heteropolyacid is prepared by heating a heteropolyacid mainly composed of oxides of tungsten at a temperature range of 150° C. to 500° C. to adjust the amount of water of crystallization contained therein to an average of 3.0 molecules or less per one molecule of the heteropolyacid.

6. The process according to claim 2 in which the heteropolyacid is prepared by heating a heteropolyacid mainly composed of oxides of tungsten in a stream of a gas inert to the heteropolyacid to adjust the amount of water of crystallization contained therein to an average of 3.0 molecules or less per one molecule of the heteropolyacid.

7. The process according to claim 2 in which the reaction is carried out under the condition that the amount of water other than water of crystallization of the heteropolyacid mainly composed of tungstenoxide is 30.0 molecules or less per one molecule of the heteropolyacid.

8. The process according to claim 4 in which the heteropolyacid mainly composed of oxides of tungsten is at least one of tungstophosphoric acid and tungstosilicic acid.

9. The process according to claim 1 in which the heteropolyacid mainly composed of oxides of tungsten is at least one of tungstophosphoric acid and tungstosilicic acid.

10. The process according to claim 3 in which the heteropolyacid mainly composed of oxides of tungsten is at least one of tungstophosphoric acid and tungstosilicic acid.

11. The process according to claim 1 in which the heteropolyacid is mainly composed of oxides of tungsten of the general formula, $$(M_1)_a(M_2)_b(W)_c(O)_d(H)_e$$

wherein $M_1$ and $M_2$ are independently metal elements, W is tungsten, O is oxygen, H is hydrogen, a is an integer of 1 or 2, b is an integer of 0, 1 or 2, c is a positive integer of 20 or less, d is a positive integer of 100 or less, and e is a positive integer of 10 or less.

12. The process according to claim 11 in which $M_1$ is an element selected from the group of P, Si, Co, Mn, Ni, As, Fe, V, and B, and $M_2$ is V.

13. The process according to claim 11 in which the heteropolyacid mainly composed of oxides of tungsten is at least one of tungstophosphoric acid and tungstosilicic acid.

14. The process according to claim 1 in which the heteropolyacid is prepared by heating a heteropolyacid mainly composed of oxides of tungsten in a stream of a gas inert to the heteropolyacid to adjust the amount of water of crystallization contained therein to an average of 3.0 molecules or less per one molecule of the heteropolyacid.

15. The process according to claim 1 in which the reaction is carried out under the condition that the amount of water other than water of crystallization of the heteropolyacid mainly composed of tungstenoxide is 30.0 molecules or less per one molecule of the heteropolyacid.

16. The process according to claim 2 in which the heteropolyacid mainly composed of oxides of tungsten is at least one of tungstophosphoric acid and tungstosilicic acid.

17. The process according to claim 11 in which the heteropolyacid mainly composed of oxides of tungsten is at least one of tungstophosphoric acid and tungstosilicic acid.

18. The process according to claim 12 in which the heteropolyacid mainly composed of oxides of tungsten is at least one of tungstophosphoric acid and tungstosilicic acid.

* * * * *